United States Patent [19]

Køhnke

[11] Patent Number: 5,163,424
[45] Date of Patent: Nov. 17, 1992

[54] DISPOSABLE RESUSCITATOR

[75] Inventor: Ole B. Køhnke, Lyngby, Denmark

[73] Assignee: Ambu International A/S, Glostrup, Denmark

[21] Appl. No.: 825,286

[22] Filed: Jan. 27, 1992

Related U.S. Application Data

[63] Continuation of Ser. No. 431,235, Nov. 3, 1989, abandoned.

[30] Foreign Application Priority Data

Nov. 4, 1988 [DK] Denmark .............................. 6196/88

[51] Int. Cl.⁵ .................................................. A62B 7/00
[52] U.S. Cl. ........................... 128/205.13; 128/203.11; 128/205.24
[58] Field of Search .................. 128/202.28, 202.29, 128/203.11, 204.18, 204.28, 204.29, 205.13, 205.14, 205.17, 205.24

[56] References Cited

U.S. PATENT DOCUMENTS

| | | | |
|---|---|---|---|
| 3,046,978 | 7/1962 | Lea | 128/205.13 |
| 3,083,707 | 4/1963 | Seeler | 128/29 |
| 3,216,413 | 11/1965 | Mota | 128/205.13 |
| 3,262,446 | 7/1966 | Stoner | 128/205.13 |
| 3,473,529 | 10/1969 | Wallace | 128/145.7 |
| 3,610,236 | 10/1971 | Smilg | 128/145.8 |
| 3,827,440 | 8/1974 | Birch et al. | 128/351 |
| 4,029,093 | 6/1977 | Kohnke | 128/145.7 |
| 4,077,404 | 3/1978 | Elam | 128/205.13 |
| 4,088,131 | 5/1978 | Elam et al. | 128/205.13 |
| 4,374,521 | 2/1983 | Nelson et al. | 128/205.13 |
| 4,501,271 | 2/1985 | Clifton et al. | 128/205.13 |
| 4,774,941 | 10/1988 | Cook | 128/205.13 |

FOREIGN PATENT DOCUMENTS 0139363 5/1985 European Pat. Off. .
293574 9/1953 Switzerland .
2139099 11/1984 United Kingdom .

OTHER PUBLICATIONS

Intertech Brochure No. B8701, "15M on Safe Response Mouth-to-Mouth Mask", Intertech Resources, Inc. 2275 Half Day Road, Suite 175, Banockburn, Ill. 60015.

Primary Examiner—Edgar S. Burr
Assistant Examiner—Aaron J. Lewis
Attorney, Agent, or Firm—Watson, Cole, Grindle & Watson

[57] ABSTRACT

A disposable resuscitator includes an elongated, elastically compressible squeeze bag having a first opening, a one-way valve for the intake of oxygen-containing gas into the bag mounted in the first opening, a second opening which is in airtight communication with a valve housing in the form of a transparent pipe having a pipe stub for the attachment of the resuscitator to a facial mask, and an outlet for exhalation air, the tubular valve housing containing a valve including a valve seat and a disc-shaped valve body of an elastomeric material and having a centrally mounted, projecting guide pin which is axially displaceable in a hole in the valve seat, a body having a central passage forming the outlet for exhalation air being provided in the free end of the transparent pipe, the central passage being surrounded by an annular bead which is located co-axially and in contact with the valve member, the pipe stub for the attachment of the resuscitator to a facial mask extending from the side of the transparent pipe and being in communication with the zone located between the valve member and the body located in the free end of the transparent pipe.

8 Claims, 4 Drawing Sheets

DISPOSABLE RESUSCITATOR

This is a continuation of Ser. No. 431,235 filed Nov. 3, 1989, abandoned.

BACKGROUND OF THE INVENTION

This invention relates to a disposable resuscitator comprising an elongated, elastically squeezable bag having a first opening, a one-way valve for intake of oxygen-containing air mounted in the first opening, a second opening which is in airtight connection with a valve housing comprising a pipe stub, which can be connected with a facial mask, and an outlet opening for exhalation air, the valve housing containing a valve comprising a valve seat and a disc shaped valve body of an elastomeric material, the valve allowing oxygen-containing air to flow from the bag into the pipe stub when the pressure within the bag exceeds atmospheric pressure and exhalation air to flow from the pipe stub to the outlet opening when the pressure within the bag is lower that the pressure within the pipe stub.

A re-usable resuscitator constructed essentially as described above is well known see for example DK patent specification No. 151.288. This known resuscitator comprises a squeeze bag comprising a self-expanding foldable insert.

After such a known resuscitator has been used for the treatment of one patient, in order to be used for the treatment of another patient it must be dismantled, cleaned and disinfected. Since this is a time-consuming operation, and further involves the risk that the resuscitator may be re-assembled incorrectly, there is a growing interest for limiting the use of such a resuscitator to one person only and discarding it after use.

This has created a need for the development of simple and inexpensive, yet reliable resuscitators.

It has been proposed to use squeeze bags without an insert and consisting of a plastic material, and in order to reduce the freight costs, the bags of some of the known apparatus have an annular folding zone of a reduced wall thickness so as to allow one end of the elongated bag to be folded into the remaining part of the squeeze bag. A resuscitator comprising such a foldable squeeze bag is disclosed in DE patent publication No. 1.616.421.

The pipe stub of the known disposable resuscitators is located co-axially and in parallel with the longitudinal axis of the squeeze bag, and it is consequently necessary to provide an angled connecting piece between the pipe stub and the facial mask so as to allow the resuscitator to be operated by a single person by performing a rhymthic compression of the bag with one hand and by maintaining the mask in contact with the patient's face in such a manner that it covers both the nose and the mouth with the other hand.

DE patent publication No. 1.277.520 discloses a re-usable resuscitator having a valve housing located partly within the squeeze bag. The valve housing of this known resuscitator consists of two valve parts which are pressed together and which at their periphery form a flange fitting into a corresponding groove on the inner side of the bag opening. The valve located within the valve housing described consists of a circular valve disc having a centrally located pin attached to a perforated valve seat forming part of one of the two valve parts. The interior surface of the other valve part comprises an annular bead provided around the outlet opening of the valve and effectively preventing oxygen-containing gas from leaking through the outlet opening of the valve. The valve housing of the known resuscitator also comprises a pipe stub extending in parallel with the longitudinal axis of the squeeze bag.

SUMMARY OF THE INVENTION

The resuscitator of the invention includes a valve housing having the shape of a pipe of a transparent material, a disc-shaped elastomeric valve body comprising a centrally located guide pin which is mounted to be axially displaceable in a hole in the valve seat, a body having a central passage forming the outlet opening mounted in the free end of the transparent pipe, the central passage being surrounded by an annular bead mounted co-axially and in contact with the valve body, and a pipe stub which is to be connected with a mask that extends from the side of the transparent pipe and is connected with the zone located between the valve body and the body located in the free end of the transparent pipe.

Thus, the valve assembly comprises three components only, viz. the transparent pipe comprising a valve seat and a pipe stub, the valve body which is displaceable relative to the valve seat, and the body having a central passage mounted in the free end of the transparant pipe.

These three relatively simple components can easily be assembled and consequently the production costs and the costs of assembling are relatively small. Furthermore, the use of a transparent pipe and the central guide pin projecting from the valve body presents the advantage that the operator can ascertain that the valve functions correctly by visually following the movements of the pin.

Thus, the pin moves away from the squeeze bag when oxygen containing gas flows from the squeeze bag to the patient and in the opposite direction when exhalation air flows from the patient and towards the outlet opening.

The body located in the free end of the transparent pipe is preferably provided with an external thread corresponding to a thread on the inner side of the pipe at its free end. Such threads facilitate the dismantling of the body if vomit is to be quickly removed from the valve chamber.

In order to facilitate the flow of exhalation air from the type stub located on the side of the transparent pipe to the outlet opening, the valve seat is preferably convex when seen from the free end of the transparent pipe. Such a shape permits the disc-shaped valve body to move away from the body inserted in the free end of the transparent pipe during the intake of breathing gas into the squeeze bag, thus increasing the cross sectional area of the passage in which the exhalation air flows towards the outlet opening.

In a preferred embodiment of the resuscitator of the invention the edge of the second opening in the squeeze bag is preferably placed in an annular groove provided on the exterior side of the transparent pipe in a stretched state so as to obtain an airtight connection between the transparent pipe and the squeeze bag and simultaneously allowing the transparent pipe to be rotated relatively to the squeeze bag.

A particularly preferred embodiment of the resuscitator of the invention comprises a strap attached to the exterior side of the squeeze bag. This strap is preferably of such a length that an operator can introduce a hand into the zone between the exterior side of the squeeze bag and the inner side of the strap and thus is able to hold the resuscitator and simultaneously subjecting the squeeze bag to rhythmic compressions.

When using a pear-shaped squeeze bag, one end of the strap is preferably attached to the squeeze bag close to the end of the squeeze bag comprising the first opening and the opposite end of the strap is attached to the squeeze bag in a zone located halfway between the opposite end of the squeeze bag and the zone having the largest diameter.

By attaching the strap to the squeeze bag in this manner the squeeze bag will rapidly expand because the strap will generate a pull following the compression of the squeeze bag with a hand located under the strap.

The one-way valve provided in the first opening in the squeeze bag is preferably a flap valve mounted on the interior side of the squeeze bag. The flap valve may comprise a circular elastic disc which is attached to a perforated valve seat by means of a centrally located pin.

The one-way valve is preferably combined with a housing which extends outwardly from the one-way valve and is open at its free end and which is adapted to cooperate with a holder connected to a collapsible bag, two one-way valves being provided in the side walls of the housing, the first one-way valve allowing air to flow into the housing when a predetermined vacuum has been established in the housing and the second one-way valve allowing gas to flow out of the housing when a predetermined superatmospheric pressure has been established therein, and a pipe stub which can be connected with a source of oxygen-containing gas.

The oxygen-containing gas which may be introduced into the housing through the pipe stub is preferably pure oxygen, e.g., supplied from pressure vessel. When supplying oxygen directly from a pressure vessel to the inhalation air in the bag there is a risk of creating such a superatmospheric pressure in the air passages of a patient that it may endanger the patient. Such a risk is eliminated with the embodiment defined above. Thus, by introducing oxygen under pressure into the housing described through the pipe stub the oxygen will fill the collapsible bag and expand it. When the pressure within the bag exceeds the predetermined value, the oxygen will start flowing out of the collapsible bag through the second one-way valve.

Following compression of the squeeze bag, the latter will expand and a vacuum is generated within the bag. This vacuum will spread into the housing and oxygen will be sucked into the squeeze bag from the collapsible bag. At the same time the first one-way valve will open, thus permitting air to flow into the housing. By repeated use of the resuscitator a mixture of air and oxygen in a ratio determined by the oxygen flow and the compression volume and operational sequence of the squeeze bag will be supplied to the patient.

The squeeze bag preferably comprises an annular folding zone located at such a distance from the second opening of the squeeze bag that the intermediate portion of the bag and the transparent pipe can be folded into that portion of the squeeze bag which is located between the folding zone and the first opening in the squeeze bag.

The folding zone preferably is a zone of reduced thickness delimited by two annular grooves provided in the exterior side of the squeeze bag.

DESCRIPTION OF THE PREFERRED EMBODIMENT

Figure 1:
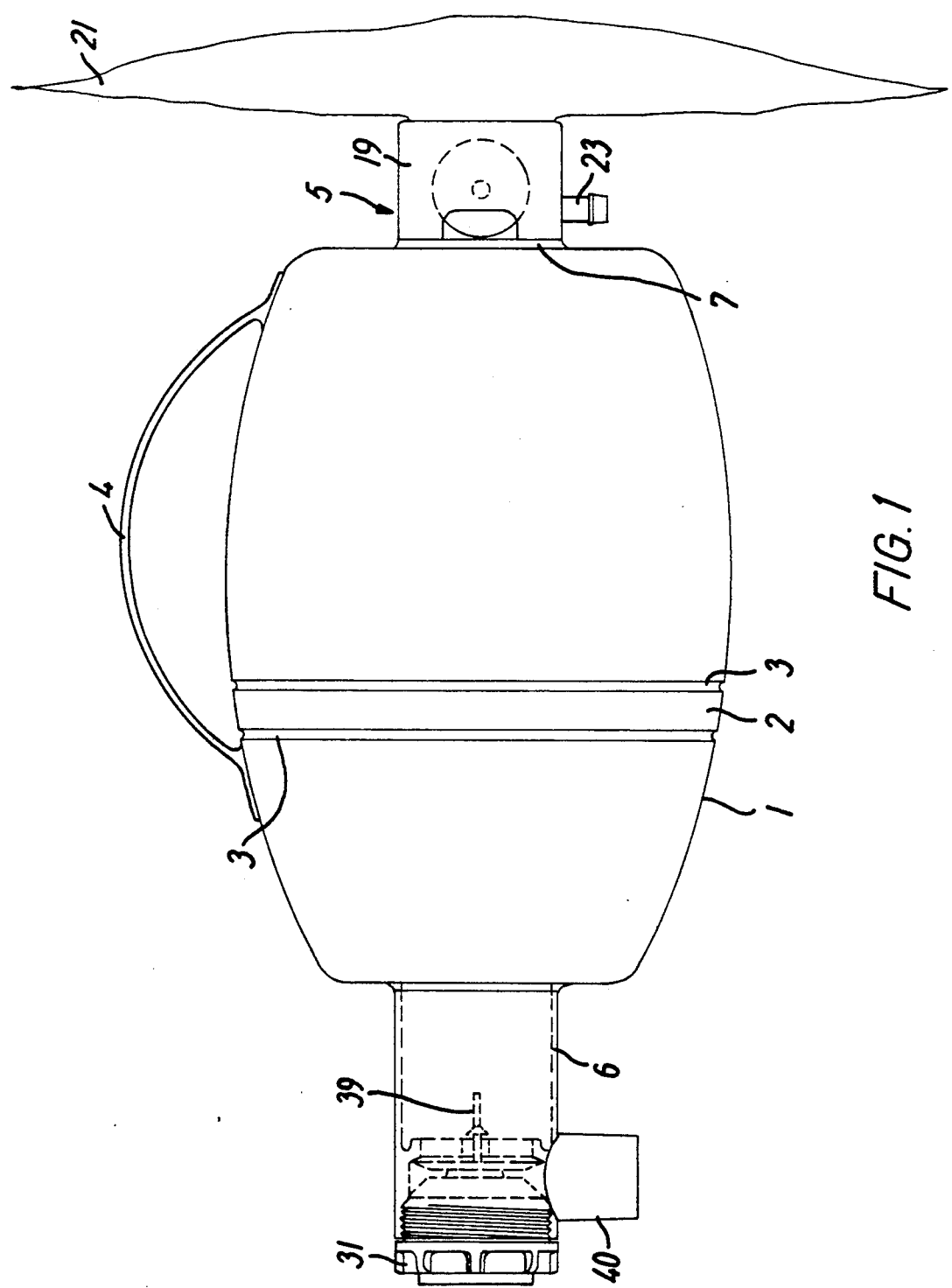
FIG. 1 shows a side view of a preferred embodiment of the resuscitator of the invention.
Figure 2:
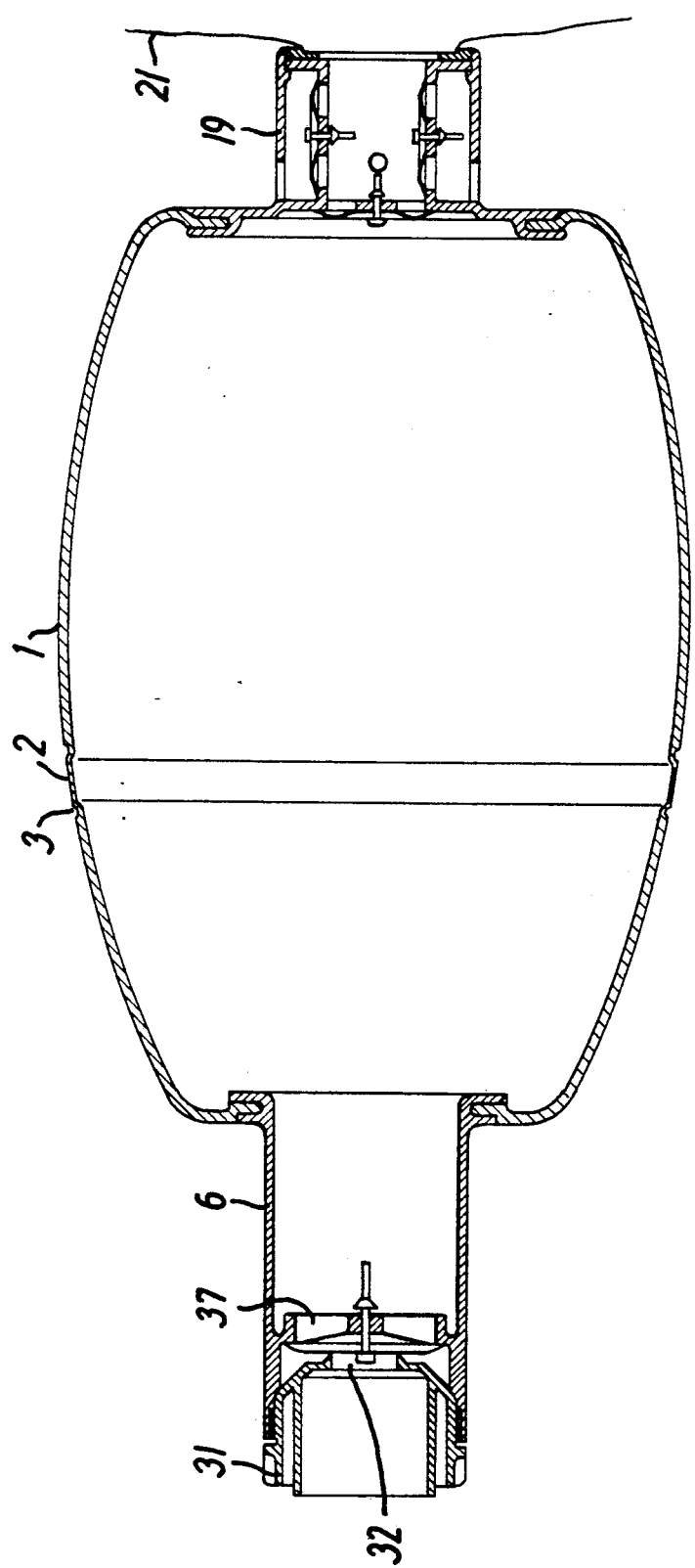
FIG. 2 shows a longitudinal sectional view of the resuscitator shown in FIG. 1 perpendicularly to the plane of the paper.

FIG. 1 shows an elongated, elastically compressible squeeze bag which is circular in cross section and which comprises an annular folding zone 2 of reduced wall thickness, the folding zone 2 being delimited by two annular and parallel grooves 3 on the outside of the squeeze bag 1. The resuscitator also comprises a strap 4 which is attached to the squeeze bag 1 at its ends.

The squeeze bag comprises an opening at each end, the first opening having intake means 5 and the second opening having a transparent pipe 6 inserted therein.

The intake means 5 consists of a circular disc 7 having along its periphery an annular groove which surrounds the edge of the opening, this edge being maintained in the groove 8 in a stretched state. The central part of the disc 7 has the shape of a valve seat with holes 9 which are covered by a thin circular elastic valve flap 10 located on the interior side of the disc 7 and which is attached to the valve seat by a centrally located pin 11. The exterior side of the disc 7 is integral with a housing 12 having two parallel side walls 13 with holes 14, these side walls forming valve seats for an intake valve mounted on the inside of the housing 12 and a relief valve mounted on the outside of the housing 12, respectively.

The intake valve comprises in addition to the holes 14 a thin circular valve flap 15 which is attached to the valve seat by a pin 16. Similarly, the relief valve comprises another thin circular valve flap 17 which is attached to the valve seat by means of a pin 18. The housing 12 is open at the end opposite to the disc 7 and, in the embodiment shown in the drawing, a holder 19 which overlaps the edges of a disc 20 attached to the mouth of a thin plastic bag 21 is attached to the free end of the housing 12. The holder 19 surrounds the housing 12 and the holder walls comprise holes 22 for intake and discharge of air and oxygen-containing gas, respectively.

The housing 12 also comprises a pipe stub 23 for attachment of a tube for the supply of oxygen to the housing.

The transparent pipe 6 comprises at one end an annular groove 30 surrounding the edge of the second opening in the squeeze bag 1, this edge being in a stretched state. A hollow member 31 having a central passage 32 surrounded by an annular bead 33 is screwed into the opposite end of the pipe 6. When there is an atmospheric or superatmospheric pressure within the squeeze bag 1, the bead 33 is in contact with a flexible elastic circular valve flap 34 having a central pin 35 which is inserted in a hole in a convex valve seat 36 with holes 37. The pin 35 is axially displaceable in the hole mentioned above and the movement in a direction away from the valve seat is restricted by a shoulder 38 on the pin 35. The pin 35 has a free end 39 and the movement of the end 39 can be observed through the wall of the transparent pipe 6.

The branch pipe 40 is provided on the side of the transparent pipe 6 and the interior of the branch pipe 40 communicates through a hole 41 in the pipe wall with a space 42, which on one hand is delimited by the valve flap 34 and on the other hand by the hollow body 31.

Figure 3:
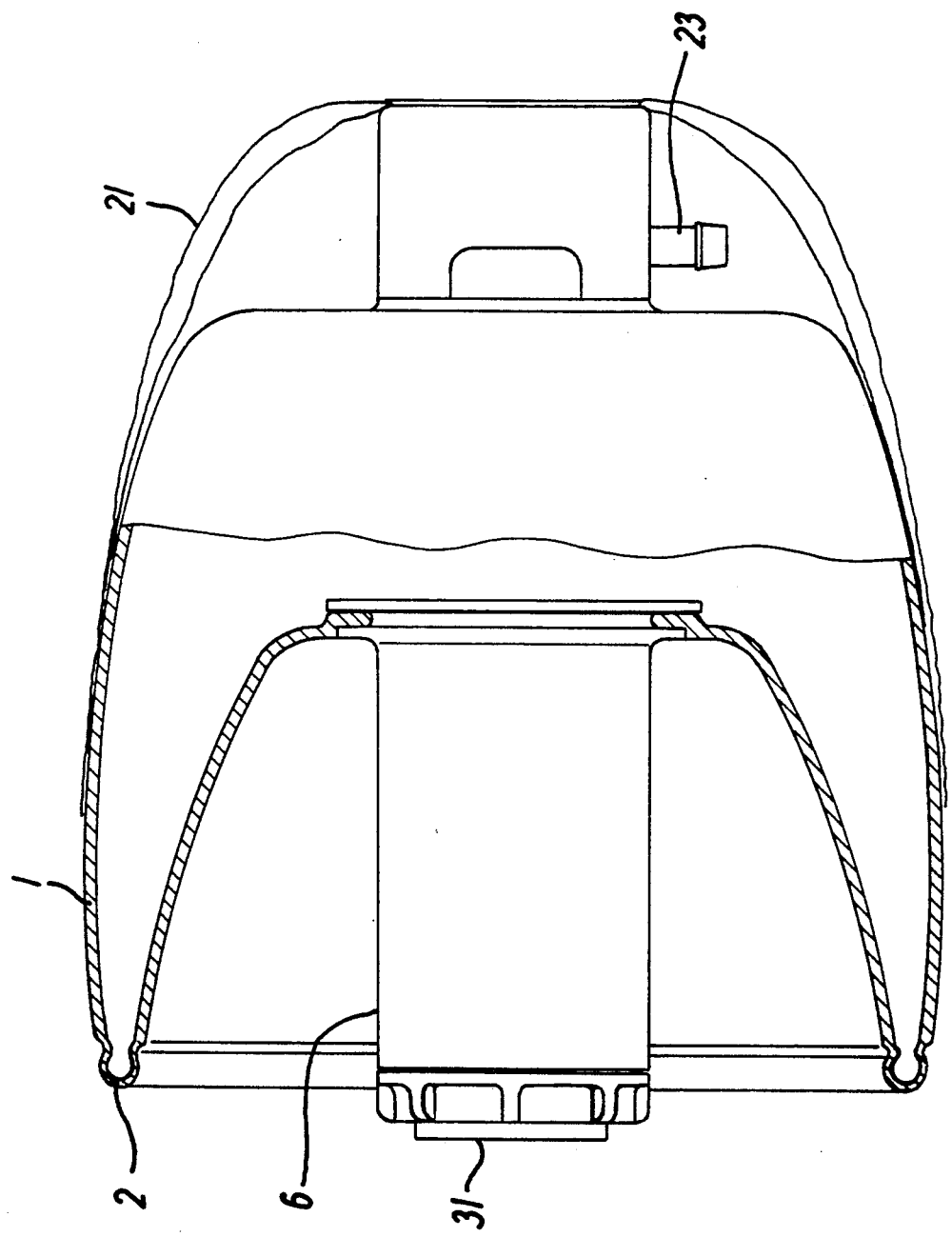
FIG. 3 shows a side view partly in section of a resuscitator of the invention in a folded state.
Figure 4:
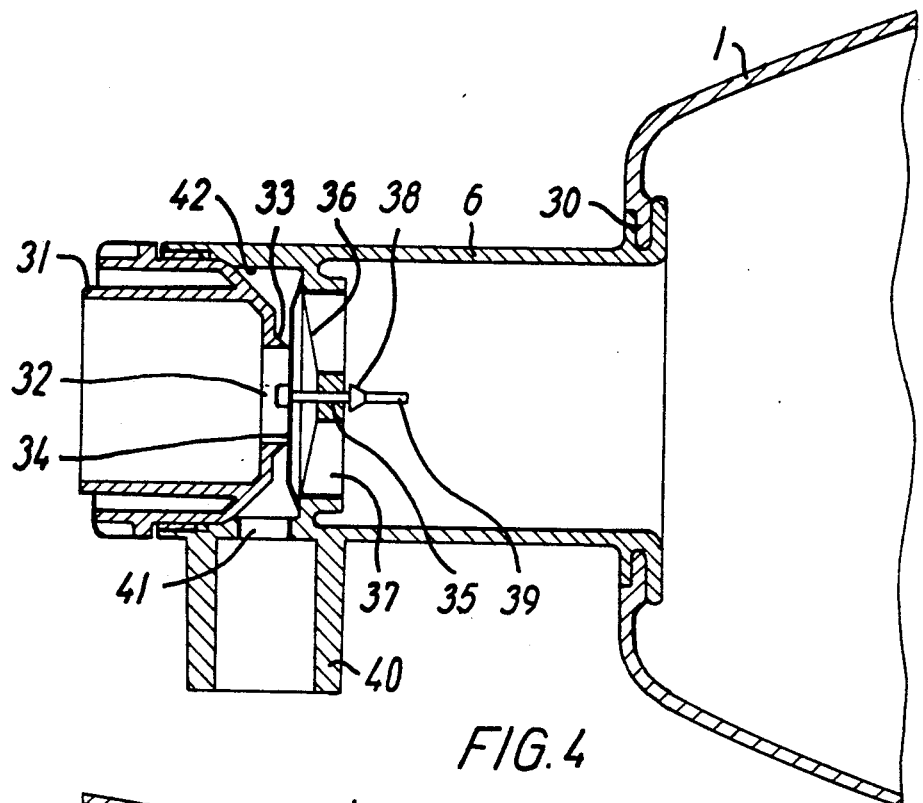
FIG. 4 shows an enlarged sectional view of the valve arrangement at the left end of the resuscitator shown in FIG. 2.
Figure 5:
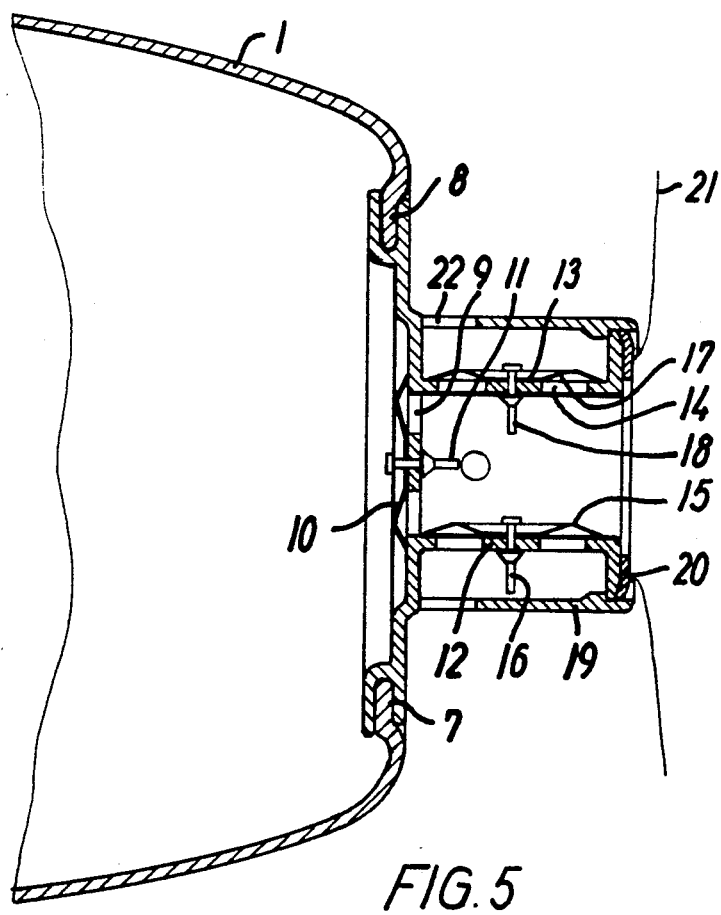
FIG. 5 shows an enlarged sectional view of the valve arrangement at the right end of the resuscitator shown in FIG. 2.

As will appear from FIG. 3, the resuscitator can be folded and placed in such a manner that it almost totally fills the interior of a box.

The resuscitator shown can be operated in the following manner:

After having placed a hand in such a manner that the strap 4 overlaps the hand, the user is capable of subjecting the squeeze bag 1 to rhythmic compressions with one hand only. The compression of the squeeze bag 1 produces a gas flow from the squeeze bag 1 into the transparent pipe 6. The pressure increase thus produced causes the valve member 34 to be displaced relative to the valve seat 36 and to be pressed against the annular bead 33, thus permitting the gas to flow through the openings 37 in the valve seat 36 into the space 42 and from the space 42 through the hole 41 and the pipe stub 40 towards a mask (not shown) connected with the pipe stub 40.

When the compression of the squeeze bag 1 ceases, the bag 1 will tend to regain its original shape, which tendency is supported by the tension generated by the strap 4. During the expansion of the squeeze bag 1 the pressure within the bag drops to a subatmospheric pressure and the valve body 34 will be pressed against the valve seat 36 so as to allow exhalation air to flow through the pipe stub 40, the hole 41, the space 42 and the central passage 32. Simultaneously, the superatmospheric pressure exerted on the exterior side of the valve body 10 will allow intake of air from the housing 12 through the holes 9 in the disc 7.

When the pipe stub 23 is connected with a source of pressurized oxygen, the oxygen will flow constantly into the housing 12 and into the bag 21. When the bag 21 has been filled with oxygen and a slight superatmospheric pressure has been established therein, the relief valve in the housing 12 will open and excessive oxygen will flow out of the housing through the holes 14 and out through the holes 22 in the holder 19. Thus, during the expansion of the squeeze bag oxygen will flow into the squeeze bag until there is no more oxygen present in the bag 21. At this stage the vacuum established in the housing 12 will open the intake valve of the housing 12 and air is caused to flow into the housing 12 through the holes 14 of the intake valve.

By using the resuscitator illustrated inhalation air having a desired oxygen concentration of between 21 and 100% can be supplied to a patient.

I claim:

1. A disposable resuscitator which comprises:
    an elongated, elastically squeezable bag which has a first opening and a second opening,
    a one-way valve for the intake of oxygen-containing air mounted in said first opening,
    a valve housing connected to said second opening, said valve housing including a transparent tubular portion having a free end and a pipe stub connected to said tubular portion and to which a face mask can be attached, said tubular portion defining a valve seat having an interior opening between said pipe stub and said bag,
    an insert member attached within said free end of said tubular portion, said insert member having a central passage which defines an outlet opening at one end thereof remote from said squeeze bag and an annular bead around said central passage at an opposite second end and which is coaxial with said interior opening, and
    a disc-shaped elastomeric valve body positioned in said valve housing which defines a periphery and fixedly mounts a central guide pin so as to be movable in said interior opening of said valve seat, said periphery of said valve body being in contact with said valve seat and said valve body being in contact with said annular beam when oxygen-containing air in said squeeze bag is at atmospheric pressure, said valve body being movable with respect to said valve seat and said annular bead to allow oxygen-containing air in said squeeze bag to flow into said pipe stub when the oxygen-containing air in the squeeze bag is at superatmospheric pressure and exhalation air to flow from said pipe stub to said outlet opening when the oxygen-containing air in the squeeze bag is at subatmospheric pressure, proper movement of said guide pin relative to said valve seat being observable through said transparent tubular portion.

2. A resuscitator according to claim 1, wherein said tubular portion includes an interior thread at said free end, and said insert member includes an external thread corresponding to said interior thread.

3. A resuscitator according to claim 1, wherein said valve seat is convex when viewed in a direction away from the free end of said tubular portion.

4. A resuscitator according to 1, wherein an edge of the second opening in the squeeze bag is located in an annular groove on an outer side of the transparent tubular portion in a stretched state.

5. A resuscitator according to claim 1, including a strap attached to an outer side of the squeeze bag.

6. A resuscitator according to claim 5, wherein said squeeze bag is pear-shaped and wherein one end of the strap is attached to the squeeze bag close to an end comprising the first opening and an opposite second end of the strap is attached to the squeeze bag halfway between the opposite end of the squeeze bag and a zone with the largest diameter.

7. A resuscitator according to claim 1, wherein the one-way valve located in the first opening of the squeeze bag comprises a housing extending outwardly from the valve and being open at a free end, said free end carrying a holder with a compressible bag attached thereto, the side walls of the housing comprising two holes and a one-way valve mounted in each hole, one of said one-way valves permitting intake of air when the predetermined vacuum has been established in the housing and the second one-way valve permitting discharge of gas from the housing when the pressure therein exceeds a predetermined value, said housing further comprising a pipe stub for supplying oxygen-containing gas to the housing.

8. A resuscitator according to claim 1, wherein the squeeze bag comprises an annular folding zone which is located at such a distance form the second opening in the squeeze bag that a part of the squeeze bag which is located between the transparent tubular portion and the folding zone as well as the transparent tubular portion can be folded into a remaining part of the squeeze bag.

* * * * *